US012303173B2

(12) United States Patent
Siedler

(10) Patent No.: US 12,303,173 B2
(45) Date of Patent: May 20, 2025

(54) IMPLANT, IN PARTICULAR A SPINAL IMPLANT

(71) Applicant: SIGNUS MEDIZINTECHNIK GMBH, Alzenau (DE)

(72) Inventor: Uwe Siedler, Alzenau (DE)

(73) Assignee: SIGNUS MEDIZINTECHNIK GMBH, Alzenau (DE)

( * ) Notice: Subject to any disclaimer, the term of this patent is extended or adjusted under 35 U.S.C. 154(b) by 332 days.

(21) Appl. No.: 17/765,330

(22) PCT Filed: Oct. 5, 2020

(86) PCT No.: PCT/EP2020/077874
§ 371 (c)(1),
(2) Date: Mar. 30, 2022

(87) PCT Pub. No.: WO2021/069385
PCT Pub. Date: Apr. 15, 2021

(65) Prior Publication Data
US 2022/0330991 A1    Oct. 20, 2022

(30) Foreign Application Priority Data

Oct. 7, 2019 (DE) ...................... 10 2019 006 963.3

(51) Int. Cl.
*A61B 17/70* (2006.01)
(52) U.S. Cl.
CPC ...... *A61B 17/7082* (2013.01); *A61B 17/7037* (2013.01)
(58) Field of Classification Search
CPC ............ A61B 17/7032; A61B 17/7035; A61B 17/7037
See application file for complete search history.

(56) References Cited

U.S. PATENT DOCUMENTS 9,486,246 B2    11/2016   Biedermann
9,848,918 B2 *  12/2017   Strausbaugh ...... A61B 17/7032
(Continued)

FOREIGN PATENT DOCUMENTS

EP    2286748 A1    2/2011

OTHER PUBLICATIONS

English Translation of the International Preliminary Report on Patentability Dated Apr. 12, 2022, 9 Pages.

*Primary Examiner* — Eduardo C Robert
*Assistant Examiner* — Michelle C Green
(74) *Attorney, Agent, or Firm* — LUCAS & MERCANTI, LLP; Klaus P. Stoffel

(57) ABSTRACT

A spinal implant, in the form of a multi-part connection device that couples a fastening element to a connection element, including a first part formed as a bracket, which has a receptacle for a part of the fastening element, and a second part in the form of a tulip, which has, in an axially upper region, a receptacle for the connection element and surrounds the bracket receptacle in an axially lower region. When the bracket is assembled in a predefined orientation in the tulip, the bracket can be axially moved in the tulip such that, when moved towards the upper region, in a receiving position the bracket can receive the part of the fastening element, and such that, when moved towards the lower region, in a holding position the bracket is no longer able to release the received part of the fastening element. An axial guide, for providing the axial movability, includes a projection region on the face of the bracket that is outside when viewed radially, which projection region engages in a cut-out region in the face of the tulip that is inside when viewed radially. The end regions, viewed azimuthally, of which projection region are spaced apart by at least 18°. An axial lock prevents the projection region from axially exiting the (Continued)

cut-out region towards the upper region, and a rotary lock prevents the projection region from rotationally entering the cut-out region and, when assembled, prevents the projection region from rotationally exiting the cut-out region.

15 Claims, 4 Drawing Sheets

(56) References Cited

U.S. PATENT DOCUMENTS

| | | | |
|---|---|---|---|
| 2008/0294202 A1* | 11/2008 | Peterson | A61B 17/7037 |
| | | | 606/305 |
| 2010/0145394 A1 | 6/2010 | Harvey | |
| 2011/0106166 A1* | 5/2011 | Keyer | A61B 17/705 |
| | | | 606/279 |
| 2016/0361096 A1* | 12/2016 | van der Pol | A61B 17/7076 |
| 2017/0086895 A1 | 3/2017 | Barra | |
| 2018/0092678 A1* | 4/2018 | Toon | A61B 17/7035 |
| 2019/0133658 A1 | 5/2019 | Biedermann | |

* cited by examiner a) b) c)

IMPLANT, IN PARTICULAR A SPINAL IMPLANT

CROSS-REFERENCE TO RELATED APPLICATIONS

The present application is a 371 of International application PCT/EP2020/077874, filed Oct. 5, 2020, which claims priority of DE 10 2019 006 963.3 filed Oct. 7, 2019, the priority of these applications is hereby claimed and the applications are incorporated herein by reference.

BACKGROUND OF THE INVENTION

The invention relates to an implant, in particular a spinal implant, in the form of a multi-part connecting device which serves for the coupling of a fastening element, in particular a pedicle screw, to a connecting element, in particular a connecting rod of a spinal support, comprising a first part in the form of a saddle, which has a receptacle for a part of the fastening element, and a second part in the form of a tulip which, in an axially upper region, has a receptacle for the connecting element and, in an axially lower region, surrounds the receptacle of the saddle, wherein, in an assembly state of the saddle already mounted in a predefined orientation in the tulip, the saddle is movable axially in the tulip such that, when moved in the direction of the upper region, said saddle in a receiving position is able to receive the part of the fastening element, and such that, when moved in the direction of the lower region, said saddle in a holding position is no longer able to release the received part of the fastening element, wherein an axial guide of the axial mobility comprises a projection region on what is the outer face of the saddle when viewed radially, which projection region engages in a recess region on what is the inner face of the tulip when viewed radially, wherein the end regions, when viewed azimuthally, of the projection region are spaced apart by at least 18°, preferably at least 24°, and comprises an axial lock which blocks the projection region against axially exiting the recess region in the direction of the upper region.

Implants of this kind are known, in particular as a spinal implant for a spinal support system, and are described, for example, in U.S. Pat. No. 9,486,246 B2. Put simply, two or more vertebrae are to be connected via a spinal support. For this purpose, a pedicle screw is screwed into a vertebra in a known manner and is rigidly coupled for example to a connecting rod via an implant of the type mentioned at the outset, and other vertebrae are in turn coupled to this connecting rod via pedicle screws and via identical or similar implants in the form of connecting devices. This rigid coupling is obtained starting from the abovementioned holding position in which, in addition, by exerting an axial force pressing the saddle against the sleeve-like tulip, which is achieved by means of a locking screw that can be screwed into the tulip and when screwed in acts directly on the saddle or indirectly on the saddle via the connecting rod, wherein, by means of for example a conical design both of the lower region of the tulip and of the receiving region of the saddle, a clamping force on the pedicle screw head is obtained and thus a rigid coupling between pedicle screw and connecting rod is achieved.

In order to insert the pedicle screw into the connecting device, the saddle is axially movable from the holding position to a receiving position. There, the receiving region of the saddle has more radial space available to it in order to expand, and in this position the receiving part of the saddle can engage around the head of the pedicle screw, for example with a clipping action. In the receiving position, the orientation of the axial alignment of the pedicle screw with respect to that of the connecting device is still freely adjustable within certain limits (polyaxial connection), and this is also true in the holding position, as long as there are still no excessive axial forces. By virtue of this design, the connecting device can be used in an expedient way, and the surgeon can achieve the correct positioning of all the components of the spinal support under the given conditions before the final fixation.

In U.S. Pat. No. 9,486,246 B2 mentioned above, the axial guide is also provided in the form of a projection on the saddle, which projection engages in a recess in the tulip. The projection is in the form of a rotary lug in order to correctly assemble the saddle with the tulip for the operational state. In the latter, incisions between side walls of the tulip, often U-shaped, and a support region of the saddle for the connecting rod, likewise U-shaped, are oriented in the assembly state in such a way that the connecting rod on the one hand passes through the U-shaped opening of the tulip and on the other hand comes to lie on the U-shaped support of the saddle. Since the pedicle screw during use is also inserted for example through a lower opening of the tulip and received by the saddle, the axial lock is provided which reliably prevents the saddle from axially emerging upward from the tulip, which in the abovementioned prior art is achieved by a shoulder which delimits the recess and against which the projection/the rotary lug of the saddle abuts. To make a connecting device of this kind ready for use, the rotary lug, starting from an orientation of the saddle with respect to the tulip rotated by 90° in relation to the operational state, is axially inserted into the tulip and then screwed into the recess of the tulip from this rotated orientation.

SUMMARY OF THE INVENTION

The object of the invention is to improve an implant in the form of a connecting device of the type mentioned at the outset, in particular in terms of its reliability.

This object is achieved by the invention through a further development of an implant of the type mentioned at the outset, mainly characterized by a rotary lock which prevents the projection region from rotationally entering the recess region and, in the assembly state, prevents the projection region from rotationally exiting the recess region.

The invention thus departs from the teaching of the aforementioned U.S. Pat. No. 9,486,246 B2 in that the inward (outward) rotation provided there for the rotary lug is specifically prevented. In the context of the invention, it has been found that in the embodiment according to the invention an increased positional stability of the orientation of tulip and saddle is achieved, hence an increased positional stability of the entire spinal support that falls back on this, which has a positive effect, in particular when the spinal support is worn for many years, and thus avoids early readjustment, which is uncomfortable for the wearer.

The explanations given at the outset regarding the polyaxial coupling, receiving position and holding position also apply to the present invention. This means that in use, i.e. during implantation, the connecting device in the assembly state can be placed onto the head of a polyaxial screw, wherein in preferred variants a receiving region of the saddle is clipped onto the screw head (in the receiving position). If screw and tulip are then forced in different directions (holding position), the lower region of the saddle abuts the lower region of the sleeve-like tulip, the pedicle screw can no longer escape axially from the lower opening of the tulip, but the head can still be turned in the receptacle, which is equivalent to the tulip pivoting in relation to the pedicle screw (polyaxial adjustment option). Only when the connecting rod inserted in the tulip/saddle has been firmly coupled, for example via a locking screw, does the clamping force from the interaction of tulip and saddle ensure that the screw head is firmly clamped and thus ensure a rigid coupling between the pedicle screw and the connecting rod of the spinal column support.

The projection region will preferably protrude from a wall-like saddle region, which itself is plane and curved, in particular of circular cross section to the axial direction. In a particularly preferred embodiment, the arc length between the azimuthal end regions of the projection region is a multiple, in particular at least twice, preferably at least three times, in particular at least four times longer than a dimension of the projection region in the axial direction.

In a particularly preferred embodiment, two axial guides of this kind, in particular arranged with a 180° offset, are provided, in particular in a symmetrical arrangement. Both axial guides together with their end regions ensure that the saddle is guided in the tulip at least in regions which, seen in cross section, lie like the end points of an "X", the center of which goes through the axial axis and whose top-bottom direction is rotated by 90° with respect to the position of the connecting rod.

In a preferred embodiment, the tulip has, in the upper region, two azimuthally spaced side walls between which the receptacle for the connecting element lies. A recess region of the axial guide is arranged in each of the side walls. These side walls are preferably likewise arcuate, in particular circular, when viewed in cross section.

A thread for screwing in a locking screw is preferably provided on the inner face of the side walls, by means of which locking screw an axial force can be exerted on the saddle, in particular via the connecting element. In principle, however, embodiments are also conceivable that have an external thread on the side walls of the tulip, with a screw cap being screwed on.

In a particularly preferred embodiment, the saddle has, on the face directed away from its receptacle, two walls which are arranged in the predefined orientation corresponding to the side walls and each carry a projection region of a respective axial guide. A free space, preferably U-shaped in axial section, is also formed between these walls, which free space can form a receiving channel for the connecting rod when brought into correspondence with a corresponding free space of the tulip.

To produce the assembly state, the saddle is inserted into the tulip from above, i.e. from the axially upper region (i.e. the side facing away from the receptacle for the part of the fastening element) in the axial direction of the axial guide (axial entry from above).

In a particularly preferred embodiment, the walls of the saddle have an elastic resilience against radially inwardly directed bending, which allows the saddle to enter the tulip axially, when the assembly state is produced, by overcoming the axial lock. This facilitates axial assembly without predominant plastic deformation of the components.

In an expedient embodiment, the thread on one or both side walls has a notch that facilitates axial entry of the saddle into the tulip. This facilitate the axial insertion while maintaining the compact design with regard to the radial dimension.

Furthermore, it is preferred that the azimuthal end regions of one projection region or of both projection regions are spaced apart by at least 30°, preferably at least 36°, in particular at least 42°. This further increases the guidance stability of the axial guide.

In an expedient embodiment, the recess region(s), when viewed in section orthogonal to the axial direction, has/have a shape that complements the shape of the projection region at some points or entirely. This avoids jamming of the axial mobility.

In a further expedient embodiment, one projection region or both projection regions, when viewed in section orthogonal to the axial direction, is/are continuous and formed in particular as a crescent-shaped projection. This facilitates the precision accuracy in the production of the saddle.

Furthermore, it is expediently provided that one projection region or both projection regions, when viewed in axial section, forms/form an in particular substantially rectangular step in an upward direction and/or a reflex step in a downward direction. This ensures low transverse forces while maintaining the intended axial lock, and yet the axial lock is easier to overcome when the assembly state is produced.

In an expedient embodiment, the walls of the saddle have on their inner face a retention bearing, in particular a thread, which serves for the coupling of an elongate instrument, which instrument serves to release the fastening element by axially holding the saddle in the receiving position when part of the fastening element is received in its receptacle.

As regards the receptacle of the saddle, it is preferably provided that this is a receptacle which holds the head of a pedicle screw, in particular by elastic clipping, and in particular a receptacle which engages beyond a region of the maximum head diameter. This ensures simplified handling when the coupling between screw and connecting device is not yet rigid.

A further component of the connecting device can be an in particular one-piece locking screw having a thread that is designed to match the thread of the side walls.

Furthermore, the invention also claims protection for an implant set having at least one connecting rod, in particular with a round cross section, at least two pedicle screws, and at least two implants according to one of the aforementioned aspects in the assembly state, in which the heads of the pedicle screws are insertable into the tulip through an opening at the end of the lower region of the latter and can be received by the receptacle of the saddle.

Such an implant set can also include an instrument having a thread matching the thread of the walls of the saddle, for holding the saddle relative to the tulip in the receiving position.

BRIEF DESCRIPTION OF THE DRAWING

Further features, details and advantages of the invention will become clear from the following description of the invention with reference to the accompanying figures, of which

DETAILED DESCRIPTION OF THE INVENTION

Figure 1:
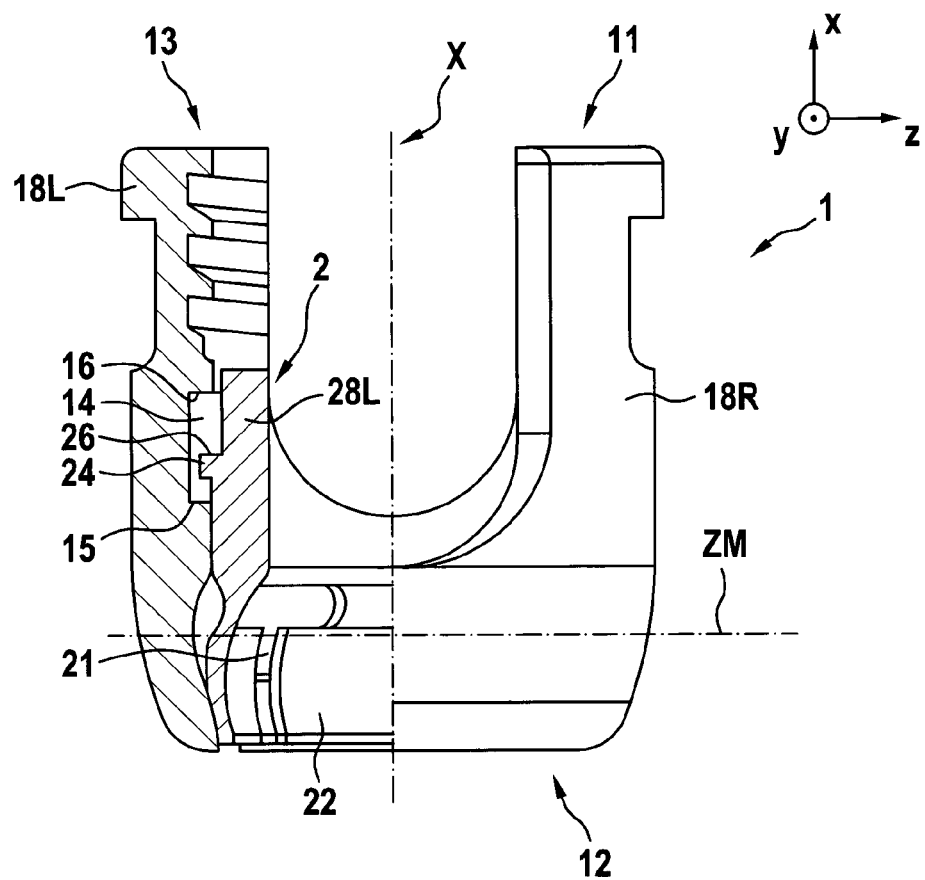
FIG. 1 shows a saddle within a tulip, in a different view in different regions.

FIG. 1 is a schematic representation of the basic structure of a part of a connecting device that is to be implanted, namely a combination of a tulip 1 and a saddle 2 arranged in the tulip 1. In the illustration in FIG. 1, the right-hand half of the picture shows a front view, while the left-hand half of the picture is divided further into an elevation view, in the right-hand region to the left of the axial axis X of the connecting device, and a sectional view on the far left of the picture.

With respect to the axial axis X, the tulip 1 forms a sleeve-shaped part with an upper end 11 and a lower end 12. Starting from the upper end 11, a U-shaped recess in the part of the sleeve wall facing toward the viewer and in the part facing away from the viewer forms a channel with a course direction Y perpendicular to the plane of the paper in FIG. 1. As can be seen clearly from FIG. 1 and FIG. 5a, the side walls 18L, 18R arranged laterally on both sides of the U-shaped recess (when viewed transversely to the course direction Y of the channel) comprise the recess region 14 of the axial guide. A connecting rod (not shown in FIG. 1) can be placed through this channel, which connecting rod, in a manner known to a person skilled in the art, connects a plurality of connecting devices of the type shown, which in turn are coupled to pedicle screws (likewise not shown in FIG. 1). The connecting rod can be inserted laterally (in the Y direction) or also from above along the axial direction X. The rod is fixed to the connecting device via a clamping screw (not shown), such as a grub screw, which is screwed into the inner thread 13 formed in the upper region of the tulip 1.

In its upper region, the saddle 2 likewise has a U-shaped recess which forms a channel which, in the position shown in FIG. 1 and intended for use, runs parallel to the channel of the tulip 1.

In the assembly position ready for use, as shown in FIG. 1, the saddle 2 is axially movable in the tulip 1 with an axial guide. For this purpose, a recess 14 is formed in the side walls 18L, 18R remaining in the upper region on account of the U-shaped cutout of the tulip 1, approximately halfway up the tulip 1, which recess 14 is limited in the downward axial direction by a shoulder 15 and in the upward axial direction by a shoulder 16. A projection 24 is guided in the recess 14, which projection 24 is arranged in the upper region of the saddle 2, on what is the outer face of the upper saddle wall 28L when viewed radially. It will be seen that the saddle 2, starting from its position relative to the tulip 1 as shown in FIG. 1, is axially upwardly movable relative to said tulip 1 until the upper end 26 of the projection 24 abuts the shoulder 16. In this way, an axial lock is provided which prevents further movement of the saddle 2 in the tulip 1 in the direction of the upper end 11 of the latter. The same axial guide is located on the right-hand side on the second wall 18R.

Figure 2:
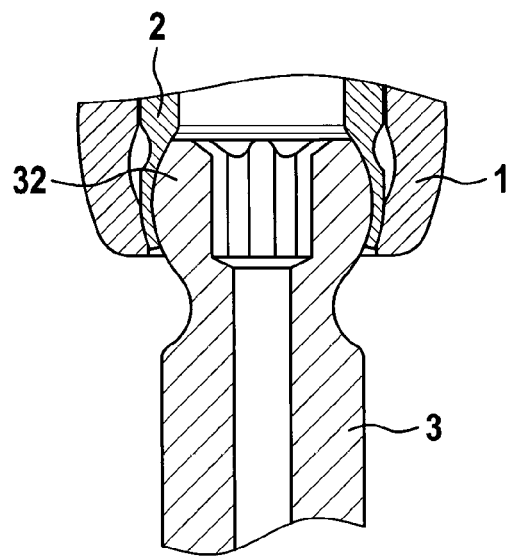
FIG. 2 shows a sectional view of a lower region of the arrangement from FIG. 1, with a held pedicle screw.

In its lower region, the saddle 2 is formed in the shape of a cup-like receptacle with holding portions 22 that are separated from one another by gaps 21. The cup-like receptacle can receive the head 32 of a pedicle screw 3 (FIG. 2). If, for example, a pedicle screw 3 has already been screwed into a vertebra, the tulip 1 with the saddle 2 lying therein can be pushed onto the screw head 32. As this is being done, the saddle 2 firstly moves upward in the tulip 1. As soon as the saddle 2 with its maximum radial dimension in the lower region reaches the region (indicated by the dashed line ZM) in which the tulip 1 has an inner curvature giving a larger internal diameter than at the lower end 12, the holding portions 22 can bend radially outward with elasticity, receive the screw head 32 in the manner of a clip and, with the screw head 32 received, can engage over the latter beyond a region of maximum diameter of the screw head.

In this position known to a person skilled in the art, the orientation of the screw axis with respect to the axial axis X can, starting from a parallel position, be pivoted in each spatial direction at any rate by a certain angle (polyaxial coupling before the rigid securing between pedicle screw 3 and connecting device).

According to a mechanism likewise known from the art, the ultimately desired rigid coupling between the connecting device, composed of tulip 1 and saddle 2, and the pedicle screw 3 is achieved by the fact that the clamping screw screwed into the thread 13 presses the saddle 2 in the tulip 1 downward via the connecting rod until, on account of the in particular conical narrowing of the opening of the tulip 1 in the lower region toward the lower end 12, the holding portions 22 are forced radially inward and hold the screw more and more firmly until the rigid coupling (conical clamping) is obtained, which is achieved by screwing the screw (not shown) tightly into the thread 13. It will be appreciated that, when the screw is only slightly tightened and not yet fully tightened, a situation that is favorable for the implanting surgeon is achieved, in the sense that the surgeon can still modify the relative position between screw and tulip 1, by targeted use of force, while an unintentional change of position no longer occurs.

Figure 5:
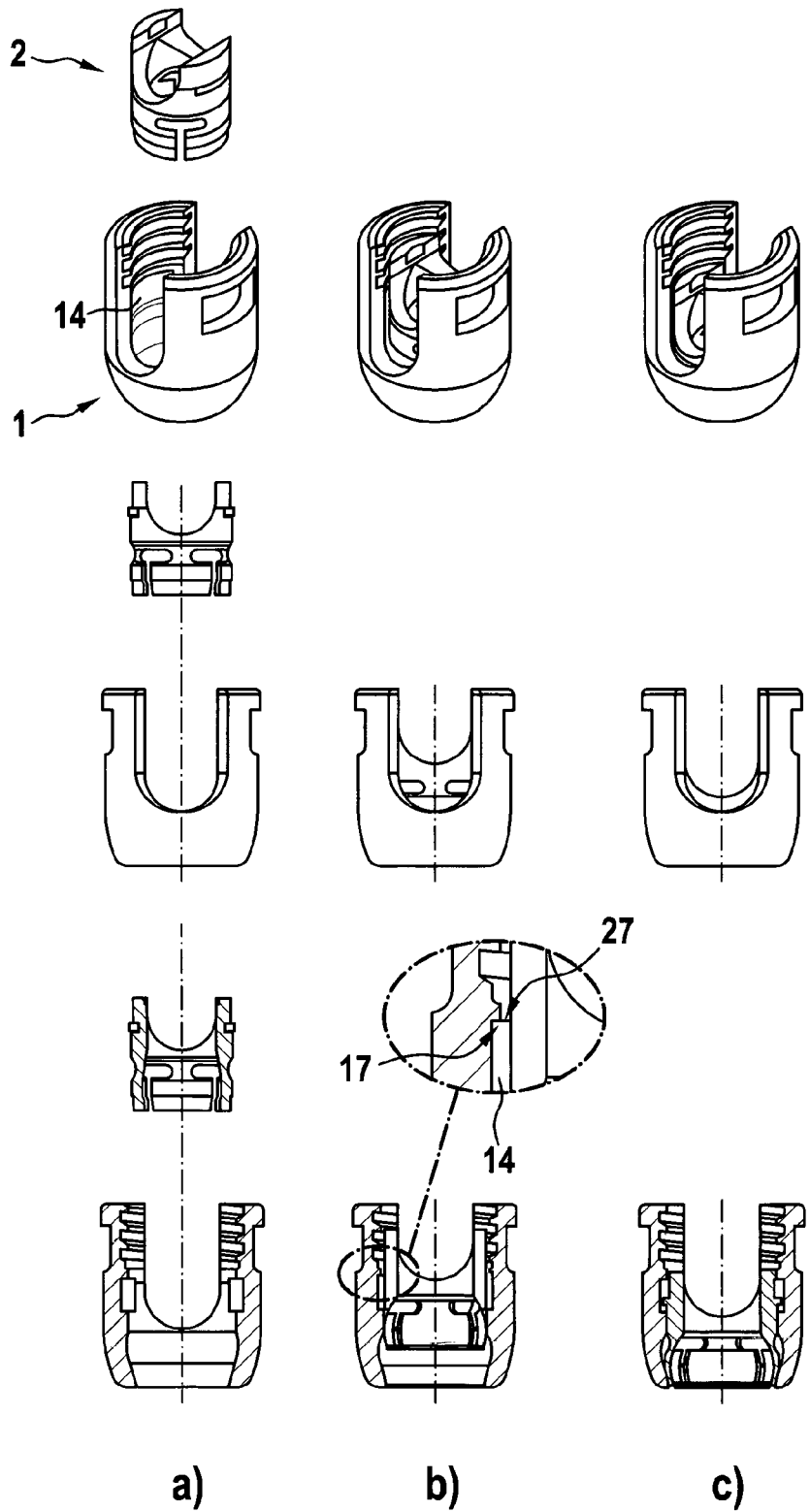
FIG. 5 shows intermediate stages of axial assembly, in a perspective view, in a front view and in axial section.

As can be seen better in the top left view in FIG. 5 in column a), the recess 14 is likewise limited in the azimuthal direction (direction of rotation in the Y-Z plane) and does not open toward the U-shaped incision between the side walls 18L and 18R. Accordingly, as can be seen in FIG. 5c and FIG. 1, the projection region 24 of the saddle 2 is received in the recess 14 in the respective side wall 18L, 18R. The rotary lock thus formed prevents rotation of the saddle 2 in the tulip 1 with axial axis X as rotation axis from the relative position shown in FIG. 1. Conversely, from a position rotated by 90° about the axial axis X in relation to the position shown in FIG. 1, the saddle 2 could also not be brought to the position shown in FIG. 1, since the rotary lock acts in both directions with respect to the azimuthal direction. The insertion of the saddle 2 into the tulip 1 cannot therefore take place via the rotation movement as in the prior art. Instead, it takes place from above along the axial axis X, as can be seen from FIG. 5a.

Figure 4:
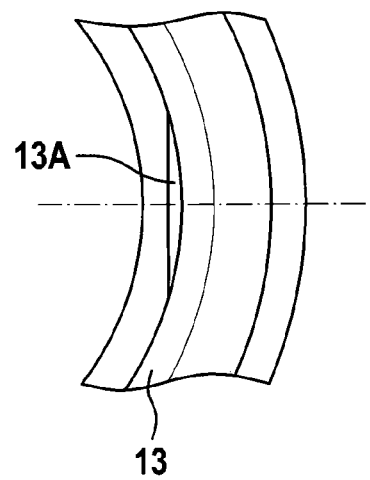
FIG. 4 shows a notch in a thread portion.

The production of this operational state shown in FIG. 1, that is to say the assembly of the components saddle 2 and tulip 1, takes place purely on an axial path, as is shown in FIG. 5. FIG. 5 shows in three types of representation, from top to bottom in a perspective view, a front view and a sectional view, intermediate stages of such an assembly procedure. The left-hand illustration of FIG. 5a) shows how the saddle 2 is arranged above tulip 1 coaxially with respect to the common axial axis X, with aligned channels formed by the respective U-shaped cutouts. Starting from this position, the saddle 2 is axially inserted into the tulip 1 through the opening on the upper face 11 of the tulip 1, initially in a manner substantially free of force and deformation, until the state shown in the middle column in FIG. 5b) is reached. For this purpose, in the illustrative embodiment shown, a cutout 13A is provided in the thread ribs of the thread 13. Furthermore, in this illustrative embodiment, the dimensional relationships in the radial direction are such that the projections 24 also at least partially utilize the space that is formed by the cutouts 13A during the axial insertion, in other words the axial insertion would be more difficult without the cutouts 13A. The cutout 13A is shown in FIG. 4 in a detail of a cross section taken at the level of a thread rib of the thread 13.

Starting from the position shown in FIG. 5b), further insertion with minimal force is no longer possible on account of the axial lock 16, 26 described above. However, by insertion then carried out by force, the walls 18L, 18R are forced radially inward with elasticity, until the resistance is overcome and the projection 24 can enter the recess 14 at the level of the shoulder 26 with elastic recovery of the walls 18L, 18R. The assembly position shown in FIG. 5c) is then reached, which corresponds substantially to FIG. 1.

Figure 3:
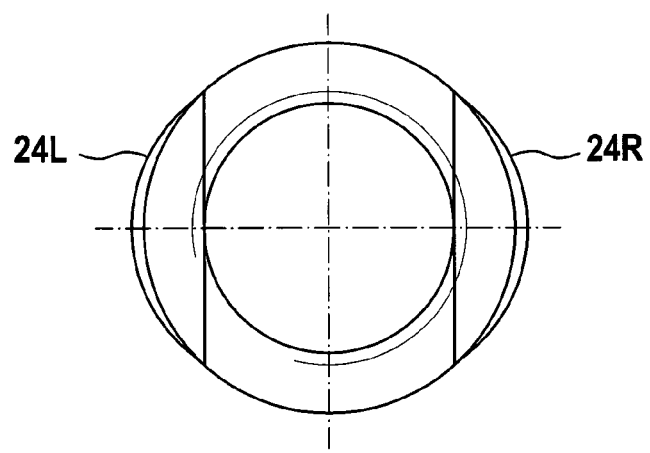
FIG. 3 is a view of the shape of projection regions of the saddle in an azimuthal plane.
Figure 6:
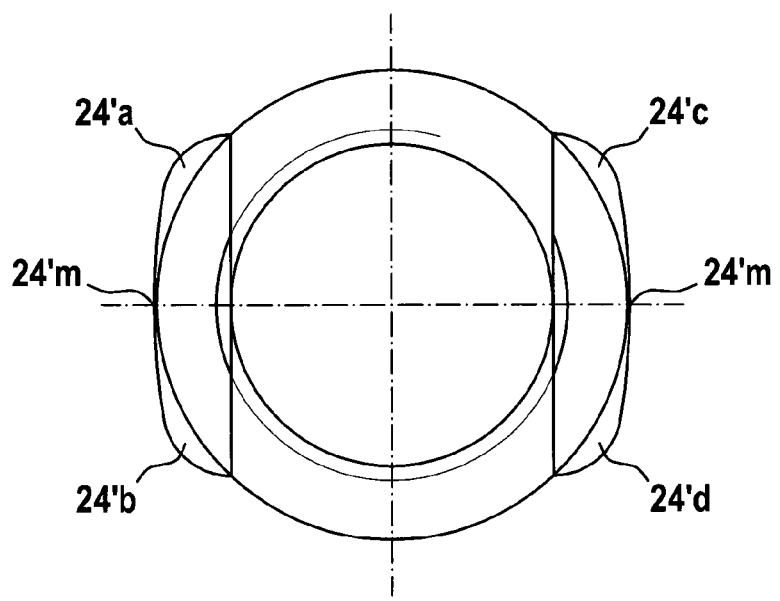
FIG. 6 shows a different configuration of projection regions than the one shown in FIG. 3.

In this illustrative embodiment (FIG. 3), the azimuthal extent of the projections 24L, 24R is approximately 50°. Irrespective of the exact shape of the projection 24, in particular in a central region between its end regions, it is preferred that the azimuthal end regions of the projection region have an azimuthal distance in the above-described ranges, in order to achieve an as far as possible positionally stable guidance of the axial guide. For this purpose, the projection region could in terms of material accumulation also be shifted more to the azimuthal end regions, with, for example as shown in FIG. 6, more weight at the end regions 24'a, b, c, d than centrally 24'm.

As can be seen in the axial section in the enlarged bottom view in FIG. 5b), the lower surface 27 of the projection 24 and the upwardly facing surface 17 of the shoulder 16 are not designed orthogonally to the axial direction X, but instead conically, in order to make it easier to overcome the axial lock when producing the assembly state. Viewed in axial section, the projection 24 can thus have a step shape in terms of its basic shape, with a substantially 90° step for the upper surface 26 and an inclined gradation to the lower surface 27 (with reflex angle).

When viewed in cross section, a crescent-shaped configuration (FIG. 3) of the projection regions is preferred. Other configurations are conceivable (e.g. FIG. 6), wherein, as has been explained above, compliance with a minimum azimuthal distance is provided.

As will be clear from the above, the invention is not limited to the embodiments described with reference to the figures. Rather, the individual features of the description and also those of the attached claims are essential to the realization of the invention in its various embodiments.

The invention claimed is:

1. An implant formed as a multi-part connecting device for coupling a pedicle screw to a connecting element, comprising:
a first part formed as a saddle that has a receptacle configured to hold a head of the pedicle screw by elastic clipping;
a second part formed as a tulip which, in an axially upper region, has a receptacle for the connecting element and, in an axially lower region, surrounds the receptacle of the saddle, wherein the tulip has, in the upper region, two azimuthally spaced sidewalls, between which the receptacle for the connecting element lies, wherein, in an assembly state of the saddle already mounted in a predefined orientation in the tulip, the saddle is movable axially in the tulip so that, when moved in a direction of the upper region, said saddle in a receiving position is able to receive the head of the pedicle screw, and so that, when moved in a direction of the lower region, said saddle in a holding position is no longer able to release the received head of the pedicle screw, wherein the receptacle for the head of the pedicle screw is configured for a polyaxial coupling, and wherein the pedicle screw is insertable through a lower opening of the tulip; and
two axial guides arranged with a 180° offset, each of the axial guides providing axial mobility and comprising a projection region on an outer face of the saddle when viewed radially, which projection region engages in a recess region on an inner face of the tulip when viewed radially, wherein the saddle, at a side directed away from the receptacle, has two walls arranged in a predefined orientation corresponding to the sidewalls of the tulip, each wall carrying the projection region of one of the axial guides, wherein end regions, when viewed azimuthally, of the projection region are spaced apart by at least 18°, and further comprises an axial lock that blocks the projection region against axially exiting the recess region in the direction of the upper region, and a rotary lock that prevents the projection region from rotationally entering the recess region and, in the assembly state, prevents the projection region from rotationally exiting the recess region, wherein the tulip and the saddle are configured to produce their assembly state by insertion of the saddle into the tulip from above when seen in an axial direction of the axial guide and thereto the walls of the saddle have an elastic resilience against radially inwardly directed bending, which allows the saddle to enter the tulip axially, when the assembly state is produced, by overcoming the axial lock, and wherein the tulip and the saddle are configured such that the receptacle of the saddle can receive the head of the pedicle screw by said elastic clipping by said insertion of the pedicle screw through the lower opening of the tulip after said axial lock is overcome by said axial entry from above and the projection enters the recess region.

2. The implant according to claim 1, wherein the end regions of the projection region are spaced apart by at least 24°.

3. The implant according to claim 1, wherein the inner face of the side walls that serves for screwing in a locking screw by which an axial force is exerted on the saddle via the connecting element.

4. The implant according to claim 3, further comprising a locking screw having a thread that matches the thread of the side walls.

5. The implant according to claim 3, wherein the thread on at least one of the side walls has a notch that facilitates axial entry of the saddle into the tulip.

6. The implant according to claim 1, wherein the azimuthal end regions of at least one of the projection regions are spaced apart by at least 30°.

7. The implant according to claim 6, wherein the azimuthal end regions of at least one of the projection regions are spaced apart by at least at least 36°.

8. The implant according to claim 7, wherein the azimuthal end regions of at least one of the projection regions are spaced apart by at least at least 42°.

9. The implant according to claim 1, wherein the recess regions, when viewed in section orthogonal to and axial direction, have a shape that complements a shape of the projection region.

10. The implant according to claim 9, wherein at least one of the projection regions, when viewed in section orthogonal to the axial direction, is continuous and formed as a crescent-shaped projection.

11. The implant according to claim 10, wherein at least one of the projection regions, when viewed in axial section, forms a substantially rectangular step in an upward direction and/or a reflex step in a downward direction.

12. The implant according to claim 1, wherein the walls of the saddle have an inner face with a thread that serves for coupling an elongate instrument, which instrument serves to release the fastening element by axially holding the saddle in the receiving position when part of the fastening element is received in the receptacle of the saddle.

13. The implant according to claim 1, wherein the receptacle of the saddle is configured to engage beyond a region of a maximum diameter of the head of the pedicle screw.

14. An implant set, comprising: at least one connecting rod; at least two pedicle screws; and at least two implants according to claim 1 in the assembly state, wherein heads of the pedicle screws are insertable into the tulip through an opening at the end of the lower region of the tulip and are receivable by the receptacle of the saddle.

15. The implant according to claim 14, further comprising an instrument having a thread matching a thread of walls of the saddle, for holding the saddle relative to the tulip in the receiving position.

* * * * *